(12) United States Patent
Ribot Barroso et al.

(10) Patent No.: US 9,968,093 B1
(45) Date of Patent: *May 15, 2018

(54) DEVELOPMENT AND MANUFACTURING PROCESS OF POWDERED ADDITIVE FOR ITS USE IN COATINGS OR SUBSTRATES TO REPEL, REDUCE AND CONTROL INSECTS

(71) Applicants: Jose Maria Ribot Barroso, Cuajimalpa de Morelos Cd. De Mexico (MX); Jose Luis Morales Martinez, San Andres Cholula Puebla (MX)

(72) Inventors: Jose Maria Ribot Barroso, Cuajimalpa de Morelos Cd. De Mexico (MX); Jose Luis Morales Martinez, San Andres Cholula Puebla (MX)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/462,806

(22) Filed: Mar. 18, 2017

(30) Foreign Application Priority Data

Dec. 19, 2016 (MX) .................. MX/a/2016/017073

(51) Int. Cl.
| | |
|---|---|
| *A01N 59/14* | (2006.01) |
| *C09D 5/23* | (2006.01) |
| *C09D 5/22* | (2006.01) |
| *A01N 53/00* | (2006.01) |
| *A01N 25/28* | (2006.01) |
| *C09D 5/14* | (2006.01) |
| *C09D 5/33* | (2006.01) |

(52) U.S. Cl.
CPC .............. *A01N 59/14* (2013.01); *A01N 25/28* (2013.01); *A01N 53/00* (2013.01); *C09D 5/004* (2013.01); *C09D 5/14* (2013.01); *C09D 5/22* (2013.01)

(58) Field of Classification Search
CPC ........ A01N 59/14; A01N 53/00; A01N 25/28; C09D 5/004; C09D 5/22; C09D 5/14
See application file for complete search history.

(56) References Cited

U.S. PATENT DOCUMENTS

2006/0086284 A1 * 4/2006 Zhang .................... A01N 55/02
106/15.05

* cited by examiner

*Primary Examiner* — Trevor Love
(74) *Attorney, Agent, or Firm* — Luoh J. Wu; Continent Patent Office LLP

(57) ABSTRACT

The innovation herein refers to a formulation of powdered additive for its incorporation in coatings or substrates to repel, reduce and control insects, consisting of at least one active insecticide ingredient, or a combination of two or more active insecticide ingredients with high-performance double microencapsulation, and alternatively with least one reflective and/or photoluminescent, high-luminosity microencapsulated pigment, generating a dual insecticide effect, preventing insects from creating immunity to insecticides, which stops mutation, as completely different insecticides are delivered overtime. It is also very effective during night and day, over long period of time (years), with an efficient manufacturing process.

1 Claim, No Drawings

DEVELOPMENT AND MANUFACTURING PROCESS OF POWDERED ADDITIVE FOR ITS USE IN COATINGS OR SUBSTRATES TO REPEL, REDUCE AND CONTROL INSECTS

This application claims the benefit of Mexico application number: MX/a120161017073 filed on Dec. 19, 2016. The content of this document and the entire disclosure of publications, patents, and patent documents mentioned herein are incorporated by reference.

FIELD OF THE INVENTION

The invention herein, including its general chemistry, is related to the field of water-based coatings formulations, such as paints, enamels, inks, sealers, polyurethane, among others. More specifically, it refers to the formulation of powdered additives with double microencapsulation and high-luminosity pigments to repel, reduce, and control insects.

INVENTION BACKGROUND

Insects are arthropods characterized by having a pair of antennae, three pairs of legs, and two pairs of wings (which can be deducted or missing). Insects are the most diverse group in the planet, and there is a huge diversity of species with around one million described species, which can be found in almost every environment in the planet.

Insects represent one of the animal classes most interrelated with human activities. From useful insects that provide us with honey or silk, up to poisonous insects, or insects that can transmit deadly diseases. There is an endless number of species that are directly or indirectly related to the human beings (Newman, L. H. 1971).

Insects play a role in the environment. They are the main predators of other invertebrates; thus, they control plagues. They decompose and eliminate a significant percentage of organic matter, and they are the main pollinizers of environmentally and economically relevant plants. Nevertheless, due to their high abundance, they are considered a harmful group, as they consume around a third of the crops at a global level, and they are the main carriers of human diseases (Brusca y Brusca, 2002).

Insects have always lived around humans, and they are a part of the ecological balance of the Earth, as they are food for birds, reptiles, and other insects. On the other hand, many insects transmit serious diseases, such as dengue, Chagas disease, zika, chikunguña, yellow fever, malaria, among other diseases; thus, being able to keep them under control is very important.

There are several insect control methods, such as biologic control, chemical control (insecticide, pesticide, acaricide, nematicide, systemic, and non-systemic insecticides, organic controls, among others.

There are insecticide products in the market such as sprays, plates, creams, and plastic and paper tapes, and anti-insects Paint, with different degrees of efficiency. Nevertheless, these products have a low residuality, and high costs, in addition to having a strong smell, and being toxic for human beings. Also, some of them contain pesticides as active ingredients, which are harmful to human health. Most of the products in the market do not comply with the claims in their labels regarding timing and functionality. These products are rather expensive; thus, they are limited to people or companies with a high purchasing power, the low-income class being the one exposed to the highest risk of infection due to insect bites.

Microencapsulation is a technique that is more and more used, and its applications have drawn the attention of many technology fields, reaching a wide range of fields, such as agriculture, the food industry, cosmetics and the pharmaceutical industry, as well as the textile and aerospace industry.

The micro-capsules release the material inside them during the preparation of other products to potentialize it or to provide a different look to it. For example, in perfumes, an essential oil is micro-encapsulated to provide a non-liquid, but rather solid, formulation, which is applied in a lower concentration, and is easier to handle.

Microencapsulation consists of applying a thin cover in small solid particles, liquid drops, or dispersions, to protect some materials, segregate them or allowing their storage and handling. This can also be done in order to release the covered substance in particular conditions, or in a prolonged, deferred way.

The conditions required for the release of a substance can be moisture, pH, physical strength, or a combination thereof. The particles contained in the micro-capsule have a size between one and 500 microns. The size can be controlled during the manufacturing process.

Microencapsulation is used to alter some of the physical properties of liquids or solids in order to protect them or make them easier to handle. This technique allows oily substances to become solid products. Substance release can be controlled, and the colloidal and superficial properties of substances can be modified.

This also allows the mixture and joint storage of substances that react, or that are incompatible with one another. This is also used to mask bad flavors or smells of substances, and it reduces the volatile characteristics of some substances.

By carrying out a search to determine the closest status of the technique, the following documents were found:

U.S. Pat. No. 6,280,759B1 by Ronald R. Price et al. was found, which was published on Mar. 7, 1989. This patent is related to micro-tubes containing an active agent inside, and compositions that contain such micro-tubes for slow and controlled release of the active agent. These micro-tubes are useful in the production of coating compositions, to protect surfaces that may come into contact with water, adhesive resins for the production of laminated, wooden products, and devices used to release pesticides. This active agent consists of one or more members selected from the group formed by fungicides, herbicides, insecticides, pheromones, hormones, antibiotics, anthelminthic, and antifouling agents.

U.S. Pat. No. 6,881,248B2 was also found, it belongs to Han Lim Lee et al, from Dec. 10, 2002, which is related to a paint composition that can counteract the development of resistance to insecticides in insects, which contain 25 mg to 50 mg of deltamethrin per liter of paint used as first component, 12.5 to 1350 mg of piperonyl butoxide per liter of paint used, and paint, in emulsion, as the third component.

U.S. Pat. No. 5,931,994A by Maria Pilar Mateo Herrero published on Dec. 23, 1996 was also found, which is related to a paint composition used to control plagues and allergens through a chitin synthesis inhibitor, which consists of a mixture from 10 to 40% of weight in water, 5 to 50% of weight in resin, 0.001 to 40% of weight in chitin, 0.001 to 5% of weight in an organophosphate, 1 to 40% of weight in a pigment, 1 to 60% of weight in a carrier material, and 1 to 20% in a stabilizer, where the weight percentages are based on the total weight of the composition, the chitin inhibitor being micro-encapsulated in a resin polymer.

U.S. Pat. No. 3,400,093A by Feinberg Irving, published on Mar. 11, 1966 was also found, which mentions a procedure to manufacture an insecticide polymer, dissolving at least one organic insecticide in at least one polymerizable monomer, such as vinyl. This monomer, and other vinyl-like monomers are included in the polymerization, providing the predominant monomeric units in the polymer, dispersing such monomer in drops through a liquid, oily polymerization medium, in which such monomer is substantially immiscible, and in which such insecticide is substantially insoluble, and polymerizing such monomer by polymerization emulsion techniques, obtaining a stable polymer latex containing small polymer discrete particles, usually solid, containing such insecticide.

Nevertheless, the products mentioned in these documents have competitive disadvantages in comparison to our development, as out formulation has a dual effect in applications such as vinyl paint. This dual effect increases the performance and efficiency of the product. Thanks to this high performance, the efficacy to repel, reduce, and control flying and crawling insects is much higher.

Given the need to count on a powdered additive formulation with double microencapsulation and the incorporation of high-luminosity pigments to repel, reduce, and control insects, the invention herein was developed.

INVENTION OBJECTIVES

The main objective of the invention herein is to provide a powdered additive formulation with double microencapsulation and high-luminosity pigments to repel, reduce, and control insects, which can be applied on several substrates.

Another objective of the invention is to provide such powdered additive formulation to control insects, also offering a dual effect in applications such as vinyl paint, increasing the performance and efficiency of the product.

Another objective of the invention is to provide such powdered additive formulation for insect control, also offering low toxicity levels that do not affect human beings, pets, and/or farm animals.

Another objective of the invention is to provide such powdered additive formulation for insect control, also offering high luminosity agents, that once mixed with the insecticide components, work together to attract insects and instantly control them.

Another objective of the invention is to provide such powdered additive formulation for insect control, also offering a longer residual effect to repel, reduce, and control flying and crawling insects, with a higher efficiency, and for a longer time than other products currently found in the market.

Another objective of the invention is to provide such powdered additive formulation for insect control, to also be used in several coatings, such as paint, enamels, inks, etc., which can also be permeated, in substrates including, but not limited to: textiles, paper, plastic, wood, metal, stone, concrete, plaster, and any construction and interior design element.

Another objective of the invention is to provide such powdered additive formulation for insect control, to also allow the control of insect populations with commonly used products, such as paint for houses, hospitals, schools, harbors, airports, farms, warehouses, industrial warehouses, construction companies, hotels, public and private sector facilities, etc.

Another objective of the invention is to provide such powdered additive formulation for insect control, is to also allow a reduction in the population of mosquitos that transmit all kinds of diseases to human beings; avoiding and/or reducing the possibility of infection with these diseases, which also benefits the health system.

And all the objectives and advantages will become apparent by Reading the following description, as well as the attached compositions, which are an integral part of this document.

INVENTION DESCRIPTION

The powdered additive formulation for its incorporation in coatings or substrates to repel, reduce and control insects consists of at least one active insecticide ingredient, or a mixture of two or more active insecticide ingredients with high-efficiency double microencapsulation and, alternatively, at least one reflecting and/or photoluminescent micro-encapsulated pigment with high luminosity, generating a dual insecticide effect, very effective during day and night.

In the preferred mode of the invention, such active insecticide ingredients are selected from a group formed by organochloride, organophosphate, carbamate, pyrethrin insecticides, biorational pesticides, among others: as well as insecticides made of plant extracts.

The basic formula of the powdered additive for its incorporation in coatings or substrates to repel, reduce and control insects without luminescent pigments can control the insect population without attracting lucifuge insects with positive phototaxis, where due to the double microencapsulation, a more stable and lasting effect is achieved, and the combination of active ingredients acting simultaneously achieve the expected results.

In the case of the formulation that includes at least one reflecting and/or photoluminescent micro-encapsulated pigment, high luminosity is generated in the formulation, with a dual effect that attracts a strong attraction of insects when the product is applied, for example, on paint, on any kind of surface. Due to the luminosity derived from the mixture of the aforementioned components, it works with high efficiency and efficacy, during day and night, thanks to the high-luminosity pigments that have the main purpose of shining in the dark by charging on luminous and/or thermal power through natural or artificial sources; that is to say, with the attraction effect for lucifuge insects with positive phototaxis, it works 24 hours a day, in comparison to other traditional products that only work for 8 hours.

Some of the insects attracted by the luminescent component of the powdered additive formulation defined by at least one insecticide component, or a mixture of two or more insecticide components, with double high-efficacy microencapsulation, and alternatively with at least one reflecting and/or photoluminescent micro-encapsulated, high-luminosity pigments, include moths, flies, mosquitos, and many other lucifuge insects with positive phototaxis, which means they are naturally attracted to it.

Other insects such as cockroaches, insect maggots, have negative phototaxis, which means they will not be attracted by the luminosity of the formulation, but they will be repelled or killed by it, due to the insecticide components.

The microencapsulation of at least one active insecticide ingredient, or the mixture of two or more active insecticide ingredients, and of at least one reflecting and/or photoluminescent, high-luminosity micro-encapsulated pigment, are preferably done separately.

In the preferred mode of the invention, the microencapsulation of at least one insecticide component, or a mixture of two or more insecticide components and at least one reflective and/or photoluminescent, high-luminosity microencapsulated pigment, is performed through a microencapsulation processes by coacervation, or through an ionic microencapsulation process.

The microencapsulation comprises a rather heterogeneous set of procedures, and it applies diverse techniques and materials. There are three main stages to consider:

The core
The coating material
Characterization

In microencapsulation, the core material is formed by solid particles or small liquid drops, and their integration is performed by agitation, using adjuvants, stabilizers, antioxidants and diluents.

The coating materials used must be compatible with the final product to apply; for example, if the core of water steam action is to be protected, or if the coating must resist the extracting action of water, it must be hydrophobic, to provide a proper protecting barrier.

In the characterization, the core material is released under certain conditions that promote releasing, these conditions do not depend on moisture or pH, or pressure and mechanical strength applied on them.

The proposed micro-capsules to be designed were developed considering the following:
a.—nucleation
B.—shell hardness
c.—dispersibility
d.—pH
Variable Identification
The micro-capsules release process involves the following:
1.—minimum percentage concentration
2.—concentration of active ingredient to release
3.—medium pH
4.—type of paint to use
5.—application temperature
6.—ambient temperature
7.—roughness of surface to paint
8.—insects to eliminate
9.—endemic insects
10.—invasive insects
11.—plagues
12.—film thickness
Microencapsulation Processes Used
1.—Polymeric microencapsulation
2.—Microencapsulation by coacervation
3.—Ionic microencapsulation With the use of these microencapsulation processes, several types of micro-capsules are obtained, with different characteristics, offering several functions regarding their releasing behavior.

1. Polymeric Microencapsulation

The micro-capsule has a relatively simple morphological structure, it is formed by two clearly differentiated elements, the active core and a thin polymeric shell covering the core. Due to the polymer characteristics, a gradual release of these active ingredients is achieved, which are integrated according to the specific application requirements of the substrate into which the micro-capsules will be deposited.

The core consists of liquid substances (mineral oil), which contain the active insecticide ingredients.

The micro-capsule formation is a complex chemical-physical process through which a suspension is obtained with micro-capsules that Rank from one to several hundred micrometers. The gradual and controlled release of the micro-encapsulated actives is obtained thanks to the nature of the coating polymer.

The key element of the additive formulation is the insecticide polymeric micro-capsule, that can also contain other components, such as a photoluminescent, high-luminosity pigment, whose main charge is calcium carbonate, the polymer is a vinyl, and the insecticides vary according to the type of vector, place of application, strategy to follow to control the plague and the applicable regulations.

In any case, it is always insecticide and acaricide active principles of wide action spectrum frequently used in insecticide formulations; thus, pyrethroids are used when immediate control is necessary, as well as a significant shock effect, without long residuality. In case prolonged efficacy is necessary, instead of an immediate effect, organophosphates are used. In all cases, paint is added a crawling-insect/cockroaches-repelling insecticide.

MICRO-CAPSULE CHEMICAL DEVELOPMENT. A polymer is a chemical substance formed by macromolecules, usually of organic nature, that were formed due to the binding of repeating smaller molecules called monomers.

Thus, obtaining a formula with gradual release, which is also effective, depends on the ratio in which these two monomers are included when the resulting polymer is produced, as well as other factors inherent to the manufacturing process, such as the moment in which the insecticide actives are incorporated, and the temperatures reached.

Life stages of paint (manufacturing—liquid paint) (application—liquid/dry paint) of different kind of polymer. First, during the manufacturing stage in which the polymer is scattered in water, the hardness of its shell is low, when it is applied and it starts to dry, the hardness increases. In the case of hard polymers, the microcapsule would be so rigid that it would not allow the active ingredient to be released, unlike the soft polymers, with which the release would be so fast that the efficacy persistency would be too low. In the case of the polymer used in this invention, there is a proper balance between hardness and flexibility, achieving a high efficacy persistency through the controlled release of active ingredients.

Other steps that are just as important are the addition of loads and pigments, and the load of active insecticide and stabilizing ingredients, required to dorm the insecticide polymeric micro-capsule protecting the actives in an acid medium (pH 4-5) to maintain the chemical stability of the ingredients for a long time, as well as all the insecticide properties.

A double shell can be provided for an active ingredient, for a longer release, controlling this characteristics overtime.

Example 1 Powdered Insecticide Polymer
Microcapsules Components

Melamine
Chitosan
Glutaraldehyde
Calcium chloride
Lauryl ether sulfate
Acetic acid
Powdered/mineral oil insecticides
Propylene glycol
Distilled water

| FORMULATION | |
| --- | --- |
| PRODUCT | % |
| Melamine | 1-5 |
| Chitosan | 1-3 |
| Glutaraldehyde | 5-20 |
| Calcium chloride | 1-10 |
| Lauryl Ether Sulphate | 1-10 |
| Acetic Acid | 0.1-0.5 |
| Insecticide Oil | 1-15 |
| Propylene Glycol | 10-30 |

Methodology

1.—Weight the melamine and the active ingredient (insecticide with mineral oil), and the propylene glycol;
2.—In a reactor, add the melamine, the active ingredient and the propylene glycol homogeneously for around 30 minutes, and then add previously dispersed chitosan in a solution with acetic acid;
3.—Stir vigorously until a paste id formed, and add a sodium hydroxide solution, lauryl ether sulfate, and a little glutaraldehyde;
4.—Stir for around 30 minutes, and add the rest of the glutaraldehyde, followed by the calcium chloride;
5.—Stir the resulting mix for 40 minutes, and set for filtration. Decant of necessary. The filter paper must be washed three times with distilled water, and the resulting product is set aside;
6.—Dry the ambient or centrifuge or dry by heat at 30° C. in a stove for 24 hr.
7.—For convenience purposes, use the material scattered in aqueous solution (slurry) or use the wet powder
8.—Pack and save in sealed containers, away from the light 2. Micro-Encapsulation by Coacervation Among the microencapsulation methods, we can find the stirring or complex coacervation microencapsulation, which is appropriate for the liquid active ingredients processing, as a shell-forming polysaccharide is used as reticulation matrix, followed by the addition of other agents such as chelating agents, sequestrants, colorants and preservatives, that make the system so complex that it would have to be chemically fractioned to understand its release mechanism in the dispersed system in question, on the other hand, it is considered that the shell formed must be hard and friable at the same time, in order to release the encapsulated materials, and to make the process reversible.

The coacervation process is a partial dehydration/dissolution of macromolecules derived from two stages, one rich in polymers, and low in solvent, called coacervated, and the other low in polymers and rich in solvent, called floating.

Partial dehydration is performed under highly controlled conditions in order to avoid polymer precipitation, and in the process, several phenomena can be observed. When the solution is being stirred, there is a colloid-rich stage in scattered status, which can be observed as amorphous liquid drops.

These drops are bound in a clear, homogeneous liquid film, rich in colloids, known as coacervated film, which is deposited and produced the material for the wall of the resulting capsules. Complex coacervation produces the simultaneous dissolution of 2 polymers, modifying the pH, as the ionic charges can neutralize each other, integrating a property into the rheology of the initial solution, either increasing or reducing viscosity.

Example 2. Liquid Ingredient Micro-Capsules Preparation Mode

Process Description
1.—active ingredient emulsion
2.—matrix formation
3.—coacervated cross-linking First stage: the emulsion is generated by adding the first materials as active ingredient with enough stirring to integrate them evenly. There is no increase in viscosity of the solution, only dispersion is obtained. The polymeric matrix-forming agent is added, and stirring continues for a certain period, in order to form appropriate globules to sequester the flavor, at this point, a light viscosity is reached, which does not interfere with the established flow, the vortex is appropriate, and there is enough shear force.

Second stage: the surfactant and pH-modifying agents are added, as well as the rest of the matrix-forming agent, and the preservative. In case the micro-capsule must be pigmented, the previously dispersed colorant in water or oil is added, and stirring continues. Balance is reached, which can be observed through the increase or reduction in viscosity, and a change of color in the emulsion.

Third stage: the cross-linking agent or the agent to harden the double film formed is added, making sure the stirring is not reduced. The emulsion is reduced, as well as the viscosity, which could even disappear. Stirring continues at a much slower speed, in order not to destroy the resulting micro-capsules with a weak shell, and not to go back to the emulsion-stage reaction. In this stage, the non-reactive supernatant material can be filtered or reintegrated into the dissolution bulk to obtain the solution with the appropriate particle size for the desired applications.

3. Ionic Microencapsulation
Powdered Insecticide Micro-Capsules
Components
a.—gelatin
b.—xanthan gum
c.—glutaraldehyde
d.—calcium chloride
e.—sodium hydroxide
f.—distilled water
g.—powdered active ingredient The main physical-chemical properties of insecticides to consider for the selection of the micro-capsules are as follows:
a.—Resistance to Alkalinity Alkalinity is natural and common in almost all materials used in the construction of houses and; thus, the supports on which the anti-insects paint is going to be applied. This is a relevant factor for the application of pesticides, as most active ingredients, especially organophosphates and carbamates, are decomposed in alkaline mediums. A pH between 5 and 6 is required for these ingredients to remain relatively stable (Table A).

TABLE A

Mean life of some active insecticide ingredients in aqueous mediums.

| Active ingredient | Time to decompose (Mean life) |
| --- | --- |
| Diflubenzuron | Stable in pH between 5 and 7. Hydrolyzed at pH 9. |
| Cypermethrin | pH 9 (7 day). Stable at pH 4. Very stable in acid solutions. |
| Deltamethrin | pH 7 (8 hrs) more stable in medium acid solutions, than alkaline solutions |

TABLE A-continued

Mean life of some active insecticide ingredients in aqueous mediums.

| Active ingredient | Time to decompose (Mean life) |
|---|---|
| D-allethrin | Stable at pH 5 after 31 days. pH 7 (500 days) pH 9 (4.3 days) |
| Chlorpyrifos | At pH 10 (7 days). It is stable in neutral and lightly acid solutions. |
| Diazinon | pH 9 (136 days). pH 7.5 (185 days). pH 5 (31 days). |
| Malathion | Quickly hydrolyzed at pHs over 7. The optimal pH range is 5 and 6. |
| Permethrin | Stable at pH between 5 and 6. |
| Methyl pirimiphos | pH 8 (5 days). pH 5 (7 days). |
| Pyriproxyfen | Stable in a pH range between 4 and 9. |

The active micro-capsule release mechanisms are release by micro-capsule porosity, by thermal expansion, fracture by force, or pressure and friction.

This alkaline hydrolysis causes a large reduction of the real efficacy of the formulation and, in general, it is directly proportional to the water alkalinity, or the alkalinity of the medium with which the formula makes contact.

The micro-capsules of the invention herein maintain the insecticide active ingredients with an acid pH; thus, it is more resistant to alkalinity than other conventional paints.

b. Adherence.

Usually, exterior paint has adherence on surfaces such as concrete, cement and other mineral components frequently found on facades or walls. Nevertheless, other kind of materials can be found, on which the adherence of this paint is not satisfactory. The microcapsules of this invention do not interfere with high-adherence paint.

c. Outdoor Durability.

With this property, the capacity of the formulas to maintain their properties in the face of all kinds of external abiotic agents is measured, agents such as moisture, sunlight, temperature, pressure, and even biotic agents such as microorganisms, fungus, and other live beings.

In the case of paint, all kinds of paint suffer from deterioration, in a higher or lower degree, when exposed to the weather. The most common effects are yellowing, cracking and chalk (superficial dust is released). In order to measure its resistant to the weather, they are exposed to "accelerated aging", subjecting a sample to UV light, in more intense levels than usual, as well as variable moisture and temperature conditions. See Bureau Veritas study d. Resistance to Temperature.

This property us particularly important in insecticides with active ingredients from the pyrethroid family, as these are quickly decomposed if exposed to high temperatures. Due to its formulation, this additive with microcapsules has a higher resistance to temperature than individual conventional insecticides.

e. Wet Scrub Resistance.

This property, additional to water resistance, indicates the washability degree of any coating. It is also a way to measure the paint resistance, in case of intense rain.

In the preferred mode of the invention, as a receiving capsule (carrier) to encapsulate the microcapsules with at least one insecticide component or a mixture of two or more insecticide components and at least one reflective and/or photoluminescent, high-luminosity micro-encapsulated pigment, microsilica is used.

In the preferred mode of the invention, the formula includes calcium carbonate as powdered excipient.

Studies and investigations on the existing insecticides were carried out to determine the appropriate insecticides for the interaction with human beings, pets, farm animals and, specially, the ones that could repel and eliminate flying and crawling insects. After these studies, the optimal components for this development were determined and selected.

On the other hand, options were analyzed to increase the product mean life, as well as its effectiveness from the double microencapsulation process; vital process in which the product increases its mean life and action for over 24 months.

Below, some insecticides are described, which can be included in the formulation, among others.

| Naming | Product type | Active ingredient | Toxicity | Formulation |
|---|---|---|---|---|
| Coumaphos | Insecticide | Coumaphos | Toxic | Powder |
| Trichlorfon | Insecticide | Metrifonate | Mildly toxic | Powder |
| Boric acid | Insecticide | Hydrogen borate | Group II Mildly toxic | Powder |
| N-methyl carbamate | Insecticide | Carbamate | Group II Mildly toxic | Liquid |
| Carbofuran | Insecticide | Carbamate | Group II Mildly toxic | |
| Alphacypermethrin | Insecticide | Cypermethrin | | powder |

In the preferred modality of the invention, the powdered additive formulation for its incorporation in coatings or substrates to repel, reduce and control insects consists of micro-encapsulated cypermethrin, micro-encapsulated deltamethrin, and boric acid, as insecticide actives, photoluminescent micro-encapsulated pigment (glow in the dark pigment), calcium carbonate as powdered excipient, and microsilica as receiving capsule (carrier).

The insecticide mixes (active ingredients), their types and amounts, are handled by ranges according to the specific insects, as well as the gradual release effect.

Formulation example:

| Active ingredient | Amount in g | | Percentage (%) | |
|---|---|---|---|---|
| | Minimum | Maximum | Minimum | Maximum |
| Micro-encapsulated deltamethrin | 0.01 | 1.5 | 0.07 | 10.0 |
| Boric acid | 1 | 10 | 6.67 | 66.67 |
| Micro-encapsulate cypermethrin | 1 | 8.5 | 6.67 | 56.67 |
| Calcium oxide | 1 | 8 | 6.67 | 53.33 |

The invention provides a production process for the powdered additive formulation for its incorporation in coatings or substrates to repel, reduce and control insects, which consists of:

a) Microencapsulating the insecticide actives through microencapsulation by coacervation or ionic microencapsulation;

b) Incorporating, in a food grade, stainless steel container, the micro-encapsulated insecticide actives, and the microsilica for around 25 to 30 minutes at a highest revolution of 400 rpm, otherwise, the microcapsule could be broken. Only these three elements must be added first, for the gaps in the microsilica to be filled with the insecticide actives, and to make those actives durable;

c) Incorporating boric acid to the mix carefully, as the mix in the previous step is very volatile, and it can be toxic if inhaled. It is recommended to wear safety equipment at all times, and mix again at a speed of 400 rpm, for at least 20 more minutes, to obtain the optimal result;

d) Adding calcium carbonate, only to give substance to the formula. Nevertheless, calcium carbonate of the highest quality possible must be used, otherwise, it will not be easily incorporated, which can result in a bad color in the final product. The mix must be done at a speed lower than 400 rpm for 20 more minutes.

The production process of a powdered additive formulation for its incorporation to coatings or substrates to repel, reduce and control insects also consists of the following stage:

e) Adding microcapsules with, at least, one reflective pigment and microcapsules with at least one photoluminescent pigment.

In the modality in which the powdered additive formulation for its incorporation in coatings or substrates to repel, reduce and control insects is used as an ingredient in paint, 15 g of the formulation must be added per liter of water-based vinyl paint.

The useful life of the paint may vary depending on the manufacturer. In this case, it is recommended to use paint with a 5-year useful life.

For its production, special stainless steel, food grade equipment is required. This includes a mixer with sealed doors to avoid the mix volatility, with a speed regulator, as high speeds can break the microcapsule and/or generate excessive heat, which can break the microcapsule, and make the desired effect be reduced or disappear.

This innovation is oriented towards the control and reduction of diseases transmitted by insects, mainly to vulnerable classes. This is a low-cost additive, and it is compatible with 90% of paint formulas, regardless of the price or brand.

In addition, the invention provides the use of the powdered additive formulation defined by, at least, one active insecticide ingredient, or a combination of two or more active insecticide ingredients, with at least one reflective and/or photoluminescent, high-luminosity micro-encapsulated pigment, for its incorporation in coatings, paint, traditional insecticides, adhesives, binders, and other vehicles to repel, reduce and control insects.

The formulation, according to the innovation herein, contains several competitive and differentiating advantages, from the technical and processing point of view (double microencapsulation, original formula and combination with luminescent elements), as well as from the practical point of view, as this formulation has a better performance for insect control, due to its mean life, over 24 months, as well as its luminescent effect to attract lucifuge insects with positive phototaxis, also repelling insects with negative phototaxis. Lastly, from the financial point of view, our product has a lower cost, in comparison to the products in the market, and it can be used on any kind of surface, which include, but are not limited to, the following: substrates such as textiles, paper, plastic, wood metal, stone, concrete, plaster, and any construction and interior decoration element. The social benefits are high, as our invention will have an important role in plague control, and the reduction of diseases transmitted by insects.

An important part of double encapsulation is that, in the system, we incorporate the use of several micro-encapsulated insecticide elements that are released in different time lapses (two or more, depending on the number of insecticide families that are added to the formula). The release scheduled is controlled by the specific characteristics of the microcapsules used during the manufacturing process (size and shell). The benefits from this system allow the elimination of the immunity developed by insects to certain insecticides overtime, as different insecticide families are released overtime, it reduces the natural evolution of insects to generate immunity; hence, it allows an efficient plague control.

The invention has been described enough, for a person with average knowledge on the matter to be able to reproduce and obtain the results mentioned in the innovation herein. Nevertheless, any person with skills on the field can make modifications that are not written in this application, but in order to apply these modifications on a certain structure, or in the manufacturing process thereof, the matters stated in the following claims are required, such structures must be included in the invention scope.

The invention claimed is:

1. A formulation of powdered additive for incorporating in coatings or substrates to repel, reduce, or control insects comprising:

A) 0.01-1.5 g microencapsulated deltamethrin,

B) 1-10 g boric acid,

C) 1-8.5 g microencapsulated cypermethrin,

D) 1-8 g calcium oxide,

E) a photoluminescent microencapsulated pigment, and

F) a reflective microencapsulated pigment.

* * * * *